Figure 4:
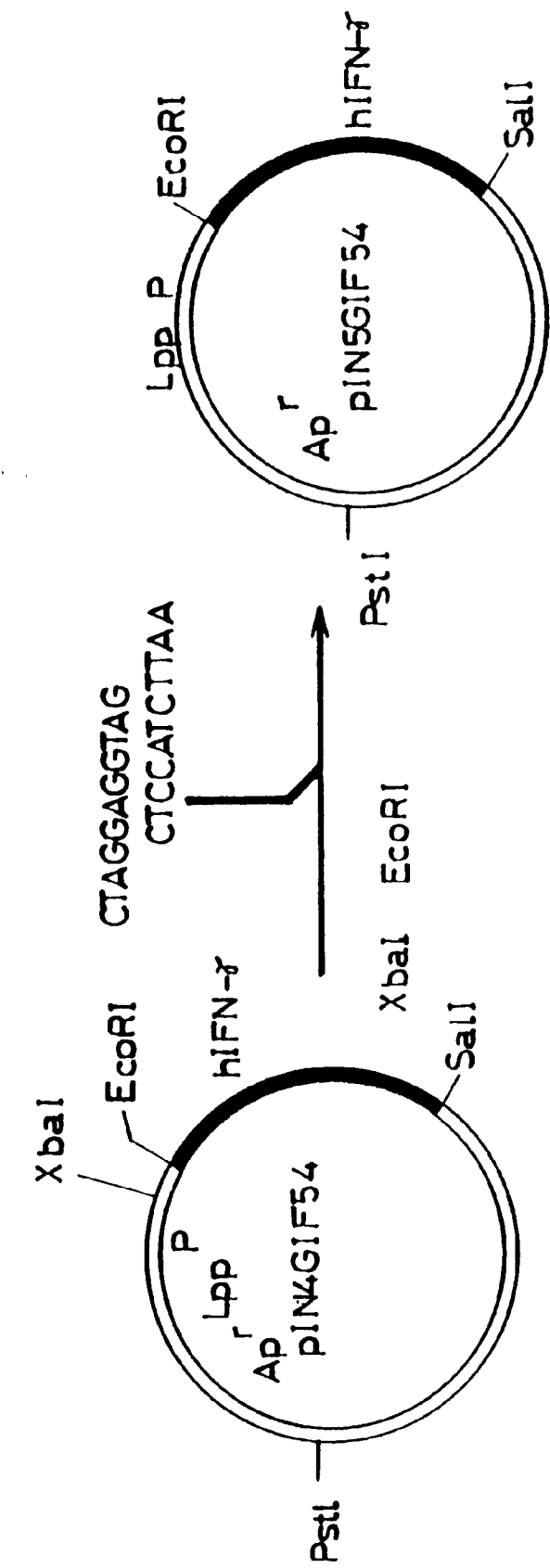

United States Patent
Ohsuye et al.

[11] Patent Number: 5,955,307
[45] Date of Patent: Sep. 21, 1999

[54] PLASMID VECTOR AND USE THEREOF FOR THE PRODUCTION OF INTERFERON

[75] Inventors: Kazuhiro Ohsuye, Ibaraki; Shoji Tanaka, Suita, both of Japan

[73] Assignee: Suntory Limited, Osaka, Japan

[21] Appl. No.: 08/915,851

[22] Filed: Aug. 21, 1997

Related U.S. Application Data

[63] Continuation of application No. 08/251,654, Jun. 1, 1994, abandoned, which is a continuation of application No. 07/842,738, Feb. 27, 1992, abandoned, which is a continuation of application No. 07/453,233, Dec. 14, 1989, abandoned, which is a continuation of application No. 06/632,204, Jul. 18, 1984, abandoned.

[30] Foreign Application Priority Data

Jul. 19, 1983 [JP] Japan ............................ 58-132524

[51] Int. Cl.[6] .......................... C12N 15/09; C12N 15/23; C12P 21/06
[52] U.S. Cl. .................. 435/69.1; 435/69.6; 435/243; 435/252.3; 435/252.33; 435/320.1; 435/471; 435/476; 536/23.52; 536/24.1
[58] Field of Search ................. 435/69.1, 69.2, 435/69.51, 69.7, 70.1, 71.1, 71.2, 172.1, 172.3, 243, 252.8, 320.1, 849, 252.3, 69.6, 252.33, 471, 476; 536/24.1, 23.1, 23.2, 23.4, 23.5, 23.52; 935/11, 13, 36, 39–41, 45, 47, 73

[56] References Cited

U.S. PATENT DOCUMENTS

| | | | |
|---|---|---|---|
| 4,315,852 | 2/1982 | Leibowitz | 530/351 |
| 4,332,892 | 6/1982 | Ptashne et al. | 435/69.7 |
| 4,762,791 | 8/1988 | Goeddel et al. | 435/365.1 |
| 4,897,471 | 1/1990 | Stabinsky et al. | 536/23.1 |
| 4,921,699 | 5/1990 | DeChiara et al. | 424/85.7 |
| 4,925,793 | 5/1990 | Goeddel et al. | 435/69.51 |

FOREIGN PATENT DOCUMENTS

| | | |
|---|---|---|
| 555226 | 11/1983 | Australia . |
| 560965 | 12/1983 | Australia . |
| 0009930 | 4/1980 | European Pat. Off. ........ C12N 15/00 |
| 0035384 | 9/1981 | European Pat. Off. ........ C12N 15/00 |
| 0077569 | 4/1983 | European Pat. Off. . |
| 0055942 | 7/1983 | European Pat. Off. . |
| 0094797 | 11/1983 | European Pat. Off. . |
| 0095361 | 11/1983 | European Pat. Off. . |
| 2091269 | 7/1982 | United Kingdom . |
| 2120255 | 11/1983 | United Kingdom . |
| 2121054 | 12/1983 | United Kingdom . |

OTHER PUBLICATIONS

Nature, vol. 287, No. 5579, Sep. 18, 1980 New York/London. D. Derynck et al. pp. 193–196.
Nature, vol. 295, No. 5849, Feb. 11, 1982, New York/London P.W. Gray et al. pp. 503–507.
Stormo et al. (1982), Nucleic Acid Research, vol. 10, pp. 2971–2996.
Backman et al. Cell 13:65–71, 1978 (Jan.).

*Primary Examiner*—Brian R. Stanton
*Assistant Examiner*—Anne-Marie Baker
*Attorney, Agent, or Firm*—Burgess, Ryan & Wayne

[57] ABSTRACT

*Escherichia coli* plasmid vectors are provided which have a 5'-terminal untranslated region (inclusive of the promoter region and Shine-Dalgarno sequence) of the *Escherichia coli* lipoprotein gene, which region is improved to thereby enable direct production of useful polypeptides in substantially complete form.

7 Claims, 8 Drawing Sheets

Construction of pIN5GIF54 Plasmid

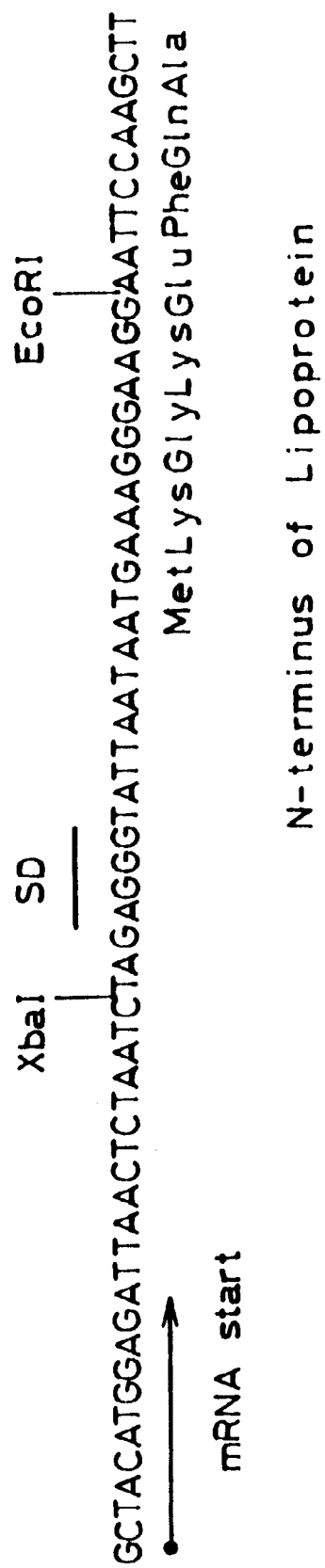
FIG. 1   pIN1-A2

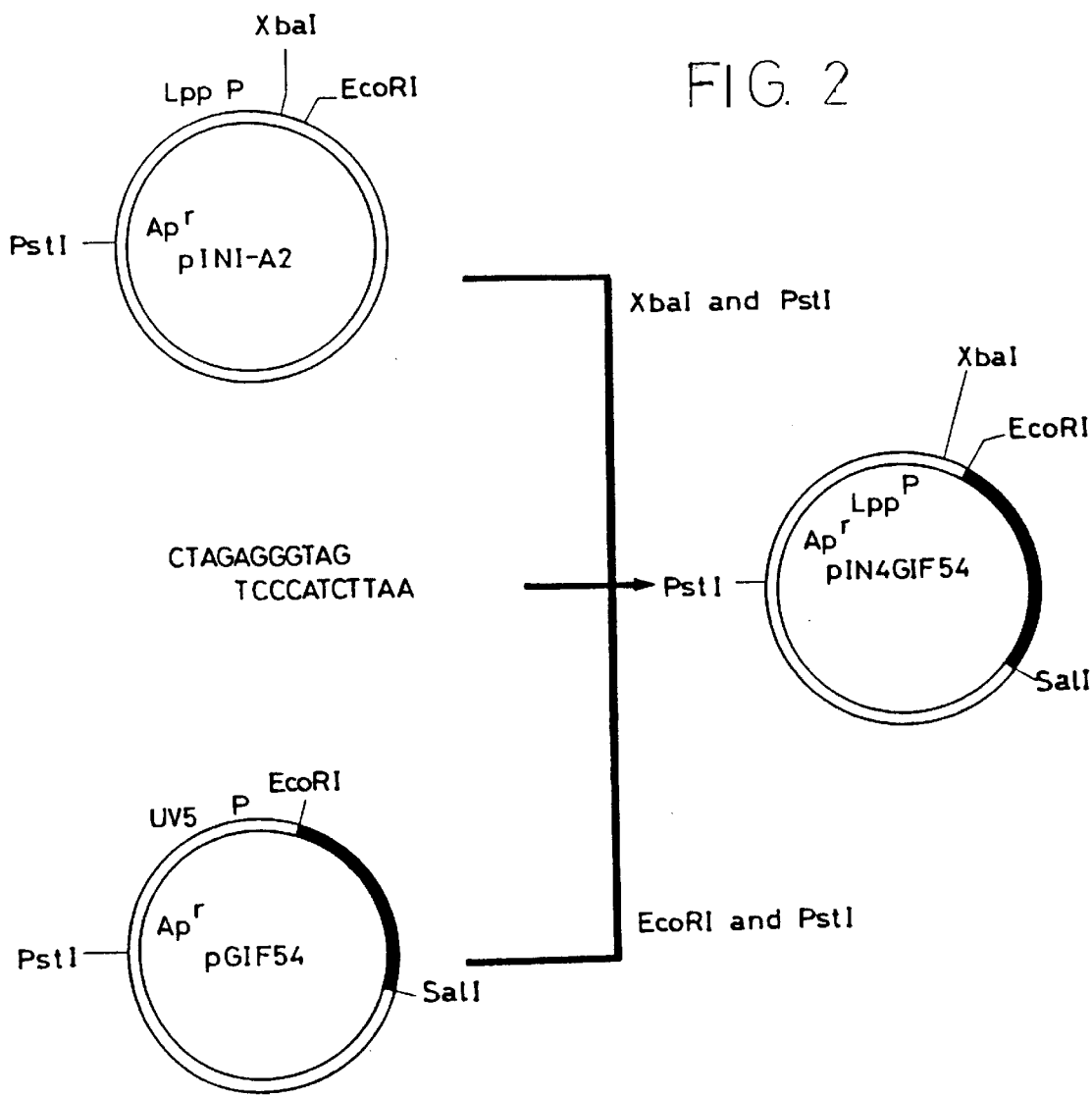

FIG. 3   pIN4GIF54

CCATCAAAAAATATTTCTCAACATAAAAAACTTTGTGTAATACTTGTAAC

GCTACATGGAGATTAACTCTAATCTAGAGGGTAGAATTCATGTGCTACTGC mRNA start

XbaI   SD   EcoRI

Linker

MetCysTyrCys

N-terminus of IFN-γ

Construction of pIN5GIF54 Plasmid

FIG. 6

```
         1                                        10                                        20
       Met Cys Tyr Cys Gln Asp Pro Tyr Val Lys Glu Ala Glu Asn Leu Lys Lys Tyr Phe Asn Ala Gly His Ser Asp
5' AATTC ATG TGC TAC TGC CAG GAC CCA TAC GTG AAG GAA GCT GAA AAC CTG AAG AAA TAC TTC AAC GCT GGT CAT TCT GAC
   3' G TAC ACG ATG ACG GTC CTG GGT ATG CAC TTC CTT CGA CTT CGA CTT TTT ATG AAG TTG CGA CCA GTA AGA CTG 30                                        40
   Val Ala Asp Asn Gly Thr Leu Phe Leu Gly Ile Leu Lys Asn Trp Lys Glu Glu Ser Asp Arg Lys Ile Met Gln
   GTT GCT GAC AAC GGT ACT CTG TTC CTG GGT ATC CTG AAA AAC TGG AAA GAA GAA TCT GAC CGT AAA ATC ATG CAG
   CAA CGA CTG TTG CCA TGA GAC AAG GAC CCA TAG GAC TTT TTG ACC TTT CTT AGA CTG GCA TTT TAG TAC GTC 50                                        60                                        70
   Ser Gln Ile Val Ser Phe Tyr Phe Lys Leu Phe Lys Asn Phe Lys Asp Asp Gln Ser Ile Gln Lys Ser Val Glu
   TCT CAG ATC GTT TCT TTC TAC TTC AAG CTG TTC AAA AAC TTC AAG GAC GAC CAG TCT ATC CAG AAA TCT GTT GAA
   AGA GTC TAG CAA AGA AAG ATG AAG TTC GAC AAG TTT TTG AAG TTC CTG CTG GTC AGA TAG GTC TTT AGA CAA CTT 80                                        90
   Thr Ile Lys Glu Asp Met Asn Val Lys Phe Phe Asn Ser Asn Lys Lys Lys Arg Asp Asp Phe Glu Lys Leu Thr
   ACT ATC AAG GAA GAC ATG AAC GTT AAG TTC TTC AAC TCT AAC AAG AAA AAG CGT GAC GAC TTC GAA AAG CTT ACT
   TGA TAG TTC CTT CTG TAC TTG CAA TTC AAG AAG TTG AGA TTG TTC TTT TTC GCA CTG CTG AAG CTT TTC GAA TGA 100                                       110                                       120
   Asn Tyr Ser Val Thr Asp Leu Asn Val Gln Arg Lys Ala Ile His Glu Leu Ile Gln Val Met Ala Glu Leu Ser
   AAC TAC TCT GTT ACT GAC CTT AAT GTA CAG CGT AAA GCT ATC CAT GAA CTG ATC CAG GTT ATG GCT GAA CTG TCC
   TTG ATG AGA CAA TGA CTG GAA TTA CAT GTC GCA TTT CGA TAG GTA CTT GAC TAG GTC CAA TAC CGA CTT GAC AGG 130                                       140         146
   Pro Ala Lys Thr Gly Lys Arg Lys Arg Ser Gln Met Leu Phe Arg Gly Arg Arg Ala Ser Gln Stp
   CCG GCT AAA ACT GGT AAG CGT AAA AGA TCT CAG ATG CTG TTC CGT GGT CGT CGT GCT TCT CAG TAA G         3'
   GGC CGA TTT TGA CCA TTC GCA TTT TCT AGA GTC TAC GAC AAG GCA CCA GCA GCA CGA AGA GTC ATT CAGCT  5'
```

PLASMID VECTOR AND USE THEREOF FOR THE PRODUCTION OF INTERFERON

RELATED APPLICATIONS

This application is a continuation of application Ser. No. 08/251,654 filed Jun. 1, 1994, now abandoned, which is a continuation of application Ser. No. 07/842,738 filed Feb. 27, 1992, now abandoned, which is a continuation of Ser. No. 07/453,233, filed Dec. 14, 1989, now abandoned, which in turn is a continuation of Ser. No. 06/632,204, filed Jul. 18, 1984, now abandoned.

This invention relates to improved *Escherichia coli* plasmid vectors which are suited for the production of useful polypeptides and to the use thereof. More particularly, it relates to improved plasmid vectors having a 5'-terminal untranslated region of the *Escherichia coli* lipoprotein gene, which region is improved in that a gene coding for a useful polypeptide can be inserted in an easy and simple manner and that said useful polypeptide can be produced in substantially complete form, and to the production of useful polypeptides using *Escherichia coli* transformants transformed with said plasmids.

The so-called recombinant DNA technology (hereinafter abbreviated as rDNA technology) has so far made it possible to produce a variety of useful polypeptides by the use of microbial cells or higher animal cells and, accordingly, it may be said that general techniques thereof have already been established. However, with respect to the technology and method of economical production of each individual polypeptide, there still remains room for improvement.

In producing a certain useful polypeptide by utilizing rDNA technology, various factors exert an influence on productivity. It is known that, among the factors the promoter involved in the promotion of transcription of an exogeneous gene coding for the useful polypeptide as inserted and the so-called Shine-Dalgarno sequence (SD sequence) involved in complementary binding of mRNA to the 3'-terminal sequence of 16S ribosome RNA have a great influence on the production of said useful peptide. However, there is no rule established between the promoter region or SD sequence and the productivity of each individual polypeptide. Thus, for instance, the fact that a certain promoter or SD sequence causes high expression of a certain heterologous gene does not always mean that it also allows high expression of another heterologous gene.

Whereas the presence of a 3'-terminal untranslated region of said gene is also a factor bringing about high expression of an exogeneous gene and is important especially for the expression of a heterologous gene in eukaryotic cells, mention thereof is not made herein because the invention has no direct relation thereto. It is also known that some host cells are suited for the expression of an objective gene but others are not suited. No further mention is made in that respect, either.

For the expression of an inserted heterologous gene, various promoters are used depending on the host cells.

When the host is *Escherichia coli,* for instance, use is made of the *Escherichia coli* tryptophan synthesis gene promoter, β-galactosidase gene promoter, β-lactamase gene promoter, alkaline phosphatase gene promoter and lipoprotein promoter and the lambda (γ) phage PL promoter, among others. Roughly speaking, heterologous polypeptides are produced by two methods. In the first method, an objective peptide is produced as a hybrid protein with a certain protein while, in the second method, the objective polypeptide is produced directly, with a methionine residue added to the N-terminus in some cases. Thus, for instance, a hybrid protein from an objective peptide and a certain protein connected with each other through methionine is produced and then treated with cyanogen bromide (CNBr) for cleaving the methionine residue, and the resulting objective peptide is isolated. In that case, use of the β-galactosidase gene promoter for producing an objective peptide as a hybrid protein with alkaline phosphatase protein is favorable in respect of productivity of the objective peptide and purification thereof (Japanese Patent Application No. 107, 474/1982). For producing polypeptides, such as interferons, by direct expression, there are used, for example, the tryptophan gene promoter, β-galactosidase gene promoter and γ phage PL promoter (cf., for example, P. W. Gray et al., Nature, 295:503, 1982; D. Goeddel et al., Nature, 287:411, 1980; T. Taniguchi et al., Proc. Natl. Acad. Sci., 77:5230, 1980; R. Derynck et al., Nature, 287:193, 1980).

On the other hand, one of the factors required for efficient production of a heterologous polypeptide in *Escherichia coli* is the SD sequence which is upstream from the translation initiation codon (ATG). The complementarity of this SD sequence and the 3'-terminal sequence of 16S ribosome RNA, the distance between the SD sequence and translation start codon, and the secondary structure of mRNA, at and around the translation startpoint, among others, are supposed to contribute to efficient initiation of translation. It is therefore presumable that the productivity of the polypeptide to be produced depends on the amino acid sequence of that portion of said peptide which is close to the N-terminus, or, in other words, the DNA sequence corresponding to said portion.

Paying their attention to the above points, the present inventors modified the nucleotide sequence of the 5'-terminal untranslated region of the *Escherichia coli* lipoprotein gene in various ways and thereby constructed *Escherichia coli* plasmids into which exogeneous genes can be inserted for very efficient expression thereof and which allow efficient production of objective polypeptides in substantially complete form, and have now completed the present invention. Furthermore, the use of the plasmid vectors according to the invention led to efficient production of a polypeptide having the amino acid sequence of human immune interferon (hereinafter abbreviated as hINF-γ), whereby culture compositions containing said polypeptide in high concentrations could be obtained.

Thus, the present invention provides *Escherichia coli* plasmid vectors characterized in that they have a 5'-terminal untranslated region (inclusive of the promoter region and Shine-Dalgarno sequence) of the *Escherichia coli* lipoprotein gene, which region is improved to thereby enable direct production of useful polypeptides in substantially complete form.

The *Escherichia coli* lipoprotein is a protein which constitutes the outermembrane of *Escherichia coli,* the content being $4.8 \times 10^5$ molecules per cell (Bacterial Outermembrane, Biogenesis and Functions, edited by Masayori Inouye, page 8, Wiley-Interscience Publication, Toronto, 1979). It is also known that the corresponding lipoprotein gene has a promoter potent in transcription activity.

The gene covering the lipoprotein promoter region (5'-terminal untranslated region) to the structural gene for said protein has already been cloned in pBR322 and a series of plasmids modified to thereby enable expression of exogeneous genes inserted therein have been constructed (cf. Kagaku to Seibutsu, 20, No. 1, 47–58, 1982). A patent specification laid open discloses heterologous polypeptide production using the above promoter region (Japanese Kokai Tokkyo Koho No. 140,800/1982).

However, the cloning vector disclosed in the above has serious drawbacks, such as mentioned below. The cloning site (site for insertion of exogeneous polypeptide-encoding genes; in said vector, the EcoRI cleavage site) of said vector is 10–11 bases downstream from the translation startpoint and therefore the desired product polypeptides have, on the N-terminus side thereof, an extra peptide added thereto. This offers a problem of antigenicity upon administration to the human body, even if the product polypeptides are physiologically active. Such polypeptides are never preferred since they have a structure different from the original one.

In accordance with the invention, novel high expression vectors free of the drawbacks that the above known vector has are constructed through modification of the SD sequence of the lipoprotein gene, modification of the distance between the SD sequence and translation startpoint and insertion of the cloning site at a new site, among others. Typical examples have proved their utility.

Hereinbelow, the plasmid vectors according to the invention and use thereof are described in more detail.

The base sequence including the *Escherichia coli* lipoprotein promoter region and part (upstream portion) of the structural gene for said protein on pINIA2, which is one of the plasmids reconstructed to thereby enable expression of exogeneous genes, is shown in FIG. 1. This plasmid has drawbacks such as mentioned above, since the cloning site (EcoRI in FIG. 1) for insertion of exogeneous genes to be expressed is in the lipoprotein structural gene (in the DNA sequence coding for the signal peptide). The base sequence from the promoter region to an upstream portion of the structural gene (to the EcoRI cleavage site) as shown in FIG. 1 is identical with that of one of the expression vectors disclosed in the above-cited Japanese Kokai Tokkyo Koho No. 140,800/1982.

Accordingly, for avoiding extra peptide addition to the N-terminus of desired heterologous polypeptides, the present inventors replaced the XbaI-EcoRI fragment shown in FIG. 1 with a chemically synthesized oligonucleotide fragment (having XbaI and EcoRI cohesive ends at the respective ends and containing the SD sequence), followed by connection of the gene coding for a desired useful polypeptide (for example, polypeptide having the amino acid sequence of hIFN-γ) downstream from said EcoRI site. The thus-constructed plasmid pIN4GIF54 was used for transformation of *Escherichia coli*. The transformant (W3110/pIN4GIF54), under the control of the lipoprotein gene promoter, could produce hIFN-γ without any extra peptide added to the N-terminus thereof.

In the above explanation, hIFN-γ has been given as an example of the heterologous useful polypeptide for better understanding. It is obvious that the above principle can also be applied to the production of other polypeptides.

FIG. 2 schematically illustrates the construction of pIN4GIF54. In the figure, pGIF54 is essentially the same plasmid as pGIF4 disclosed in Japanese Patent Application No. 86,180/1982. An *Escherichia coli* transformant, WA802/pGIF4, obtained by transformation with said plasmid containing the chemically synthesized gene coding for the amino acid sequence of hIFN-γ as shown in FIG. 6 has been named SBMG105 and deposited with the Fermentation Research Institute, the Agency of Industrial Science and Technology [Deposit No.: FERM P-6522; International Deposit No. (under the Budapest Treaty): FERM BP-282].

The plasmid pINI-A2 is a gift from Mr. Inoue of New York State University. A host *Escherichia coli* strain obtained by transformation with said plasmid has been named JA221/PINIA2 and deposited with the Fermentation Research Institute under Deposit No. FERM BP-320.

FIG. 3 illustrates the nucleotide sequence from the 5'-terminal untranslated region of the lipoprotein gene as modified according to the invention to an upstream portion of the hIFN-γ gene inserted. The SD sequence shown in FIG. 3 is the same as that of the lipoprotein gene and the distance between the SD sequence and the translation initiation codon remains unaltered.

While the strain of *Escherichia coli* transformed with pIN4GIF54 constructed in the manner shown in FIG. 2, W3110/pIN4GIF54, also produced hINF-γ (as described later in detail), the inventors attempted further modification of the SD sequence for increasing the productivity (cf. FIG. 4). Thus, they designed the SD sequence oligonucleotide so as to make it complementary to the 3'-end sequence of *Escherichia coli* 16S ribosome RNA, and chemically synthesized the DNA fragment shown in FIG. 4, namely

Then, pIN5GIF54 was constructed by replacing the XbaI-EcoRI fragment of pIN4GIF54 with the above DNA fragment. *Escherichia coli* transformed with this plasmid, W3110/pIN5GIF54, was found to produce hIFN-γ in an amount 4 times greater as compared with the case of W3110/pIN4GIF54 (cf. Table 2), indicating that the modification of the SD sequence according to the invention is effective. Furthermore, culture compositions containing hIFN-γ in high concentrations could be obtained from the cultured cells of said transformant.

In the example of the invention, ampicillin-resistant gene is inserted as a drug-resistant gene into the plasmid of the invention (ref. FIGS. 2 and 4), however, the drug-resistant gene is not limited to the example, and other known drug-resistant genes may be employed. For instance, well-known tetracycline or kanamycin-resistant gene may be used instead of the ampicillin-resistant gene without injuring the essence of the invention. In the plasmid vector of this invention, the gene coding for the amino acid sequence of human immune interferon can be a chemically synthesized gene or a gene produced with the aid of purified immune interferon mRNA from human pancreatic tissues or peripheral blood lymphocytes.

Figure 7:
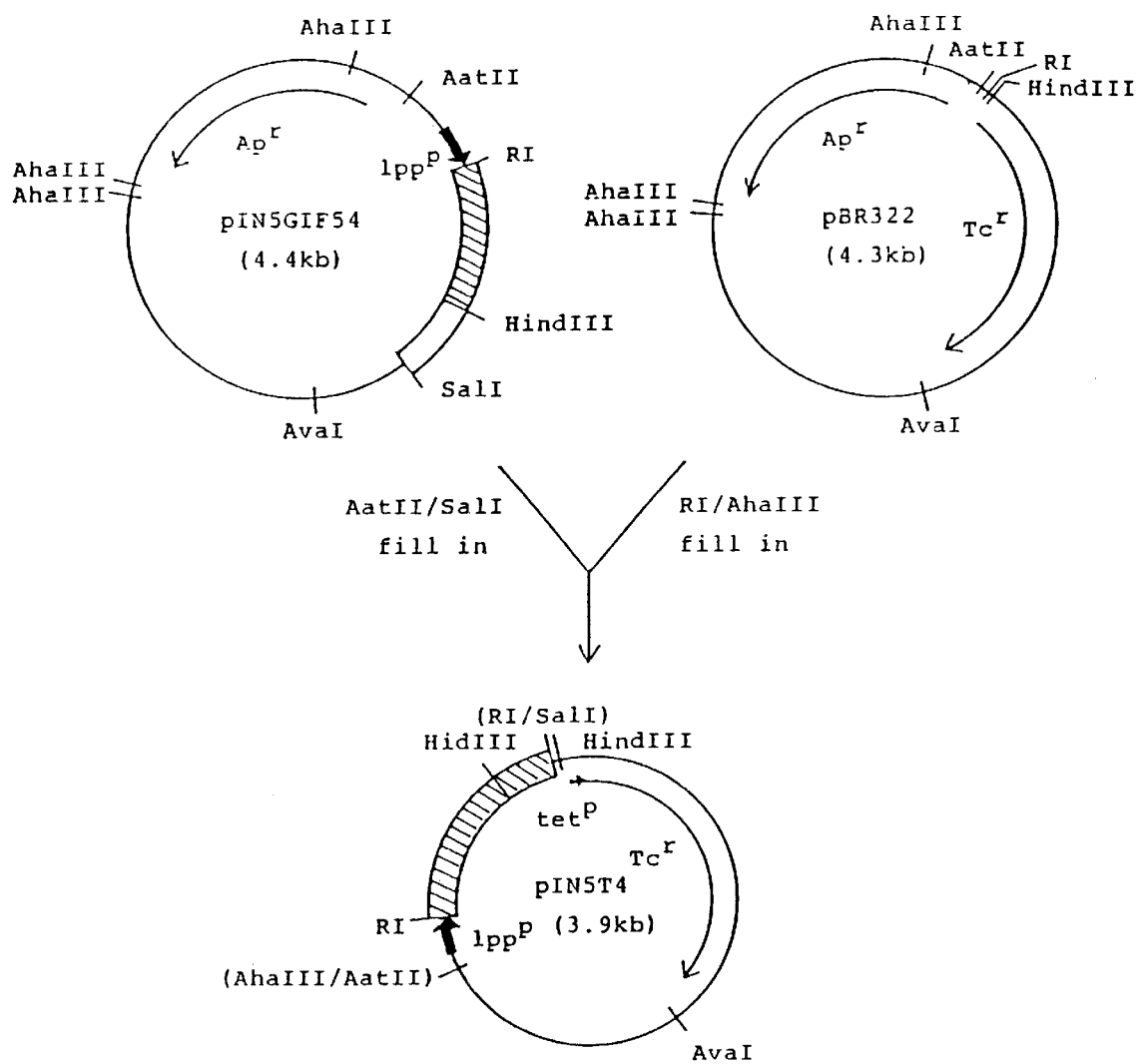
Figure 8:
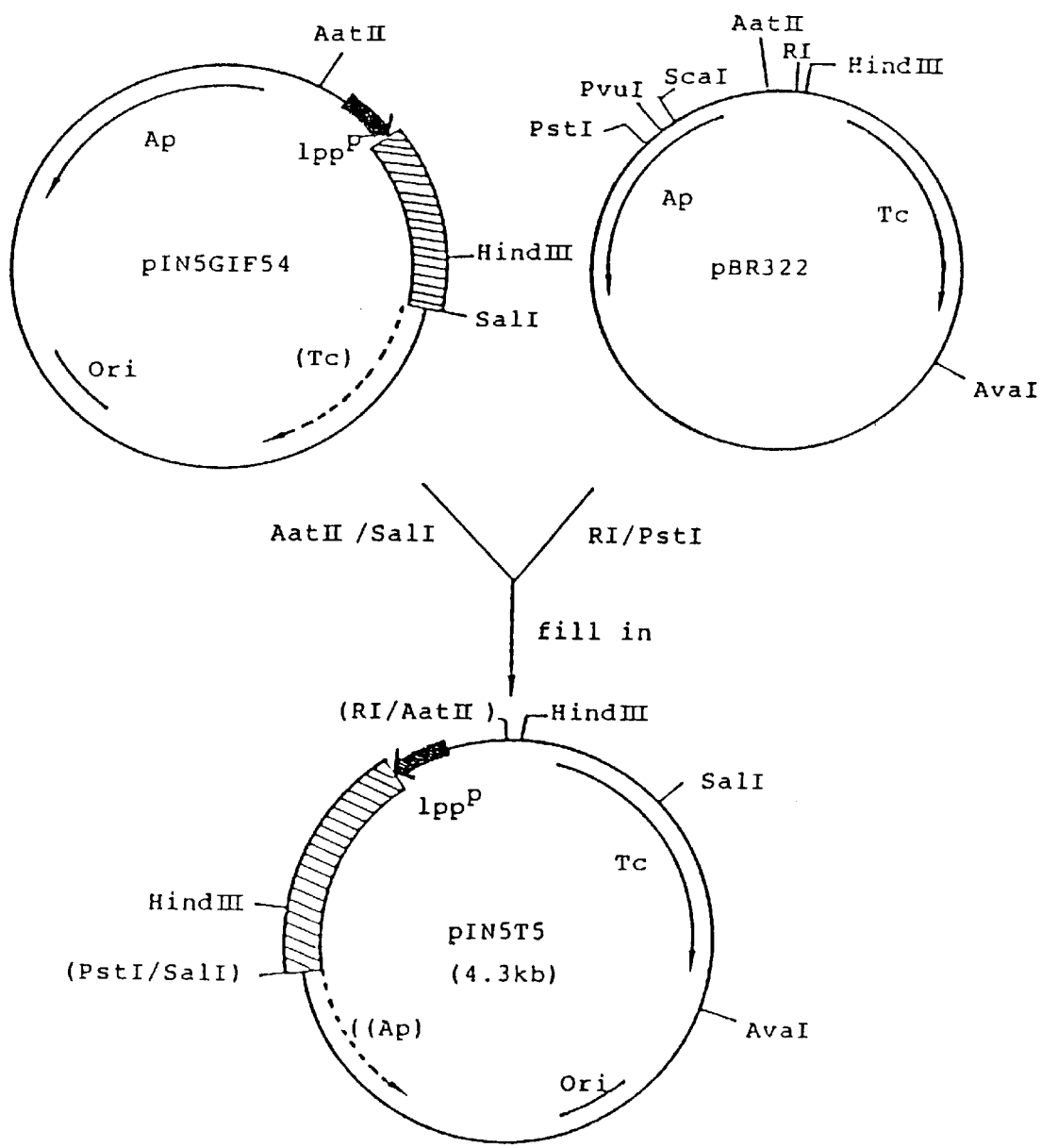

The drawings are briefly explained as follows;

FIG. 1 shows the base sequence of the 5'-terminal untranslated region of the *Escherichia coli* lipoprotein gene, which includes the promoter region and SD sequence, on the plasmid pINIA2 and part (upstream portion) of the structural gene for said protein. FIG. 2 schematically illustrates the construction of the hIFN-γ gene expression plasmid vector pIN4GIF45. FIG. 3 shows the base sequence covering the improved 5'-terminal untranslated region of the lipoprotein gene on the plasmid pIN4GIF54. FIG. 4 schematically illustrates the construction of the hIFN-γ gene expression plasmid vector pIN5GIF54. FIG. 5 shows the base sequence covering the improved 5'-terminal untranslated region of the lipoprotein gene on the plasmid pIN5GIF54. FIG. 6 shows the base sequence of a chemically synthesized hIFN-γ gene and the corresponding amino acid sequence. FIG. 7 and FIG. 8 schematically illustrate the construction of the plasmids PIN5T4 and PIN5T5, respectively.

The following examples illustrate the invention in more detail.

EXAMPLES

I. Construction of pIN4GIF54

The plasmid pIN4GIF54 was constructed, as shown in FIG. 2, from (1) DNA fragment containing the lipoprotein gene promoter region (indicated by lpp in the figure) as obtained by digestion of the plasmid pINIA2 with the restriction enzymes XbaI and PstI, (2) oligonucleotide having XbaI and EcoRI cohesive ends and (3) DNA fragment containing the hINF-γ gene as obtained by digestion of the plasmid pGIF54 with EcoRI and PstI. The procedure followed was as described hereinbelow. The restriction enzymes used were all products of Takara Shuzo K K.

A) Preparation of XbaI-PstI DNA fragment of pINIA2

The pINIA2 DNA (3 μg) was digested with 15 units each of XbaI and PstI in 150 μl of 1 X TA solution (33 mM Tris acetate buffer, pH 7.6, 66 mM potassium acetate, 10 mM magnesium acetate and 0.5 mM dithiothreitol) at 37° C. for 60 minutes. The reaction mixture was subjected to 1.0% agar gel electrophoresis and a gel portion located at the position corresponding to about 980 b.p. (base pairs) was cut out and placed in a dialysis tube, and the XbaI-PstI DNA fragment was eluted by electrophoresis. After removal of ethidium bromide from the eluate by adding an equal amount of phenol thereto, 2.5 volumes of ethanol was added. After standing at −80° C. for 30 minutes, the mixture was centrifuged at 10,000 rpm for 10 minutes, whereby the DNA fragment was obtained as an ethanol precipitate. To this ethanol precipitate was added 10 μl of distilled water for dissolving the DNA fragment.

B) Preparation of EcoRI-PstI DNA fragment of pGIF54.

The pGIF54 DNA (3 μg) was digested with 15 units each of EcoRI and PstI in 30 μl of 1 X TA solution at 37° C. for 60 minutes, followed by 0.7% agar gel electrophoresis, whereby an EcoRI-PstI DNA fragment of about 3.4 Kb was eluted from the gel. The eluate was subjected to phenol treatment and ethanol precipitation in the same manner as above. To the ethanol precipitate, 10 μl of distilled water was added for dissolution of the DNA fragment.

C) Preparation of oligonucleotide having XbaI and EcoRI cohesive ends.

For the expression of complete hINF-γ protein, an oligonucleotide having the Shine-Dalgarno (SD) sequence downstream from the XbaI cleavage site of pINIA2 and further having an EcoRI cohesive end, namely the oligonucleotide

XbaI cohesive end EcoRI cohesive end was synthesized by the solid phase method. The synthetic procedure has been disclosed in detail in U.S. patent application Ser. No. 496, 176.

The above oligonucleotide (100 picomoles) was phosphorylated at the 5'-OH in 30 μl of a kinase reaction solution (50 mM Tris hydrochloride buffer, pH 8.0, 10 mM MgCl$_2$, 10 mM dithiothreitol), with 2 units of T4 polynucleotide kinase (Takara Shuzo K K) added, at 37° C. for 60 minutes.

D) Construction of pIN4GIF54

The plasmid pIN4GIF54 was constructed by ligation of the three DNA fragments prepared above in accordance with the following procedure. Thus, to a mixture of 5 μl of a solution of the XbaI-PstI DNA fragment of pINIA2 (solution of the ethanol precipitate in 10 μl of distilled water), 5 μl of a solution of the EcoRI-PstI DNA fragment of pGIF54 (solution of the ethanol precipitate in 10 μl of distilled water) and 3 μl of a solution of the phosphorylated oligonucleotide (10 picomoles), there were added 2 μl of a ligation reaction medium 10-fold higher in concentration (20 mM Tris hydrochloride buffer, pH 7.6, 10 mM MgCl$_2$), 2 μl of 4 mM ATP and 1 μl of a solution of T4 DNA ligase (Boehringer Mannheim) (5 units), and the ligation was carried out at 16° C. overnight.

II. Transformation of Escherichia coli

A) Transformation of Escherichia coli WA802

Escherichia coli WA802 was cultured in 2.0 ml of L-broth at 37° C. overnight, 0.3 ml of the culture broth was added to 30 ml of L-broth, and shake culture was performed at 37° C. for 2 hours, followed by centrifugation at 3,000 rpm for 10 minutes. To the thus-obtained cells was added 10 ml of 50 mM CaCl$_2$ for suspending the cells, and centrifugation was conducted at 3,000 rpm for 10 minutes. To the thus-obtained cells was added 1.0 ml of 50 mM CaCl$_2$ solution, and the mixture was allowed to stand in an ice bath for 60 minutes. To 0.2 ml of this suspension of Ca++-treated cells was added 10 μl of the ligation reaction mixture obtained in Example I-D (containing the above-mentioned three DNA fragments ligated), the mixture was allowed to stand in an ice bath for 60 minutes, them 2 ml of L-broth was added and incubation was conducted at 37° C. for 60 minutes. The culture broth was used for plating a nutrient agar medium (BBL) containing 40 μg/ml of ampicillin. After incubation at 37° C. overnight, ampicillin-resistant transformants were selected. One of the transformants obtained was used for plasmid DNA separation therefrom by the conventional method (cleared lysate method). The base sequence of the DNA at and around the XbaI-EcoRI region inserted was determined by the Maxam-Gilbert method (Methods in Enzymology, 65:499–560, 1980) and it was confirmed that the DNA had the desired DNA base sequence. This plasmid was named pIN4GIF54 and the transformant Escherichia coli strain carrying the same was named WA802/pIN4GIF54.

Figure 5:
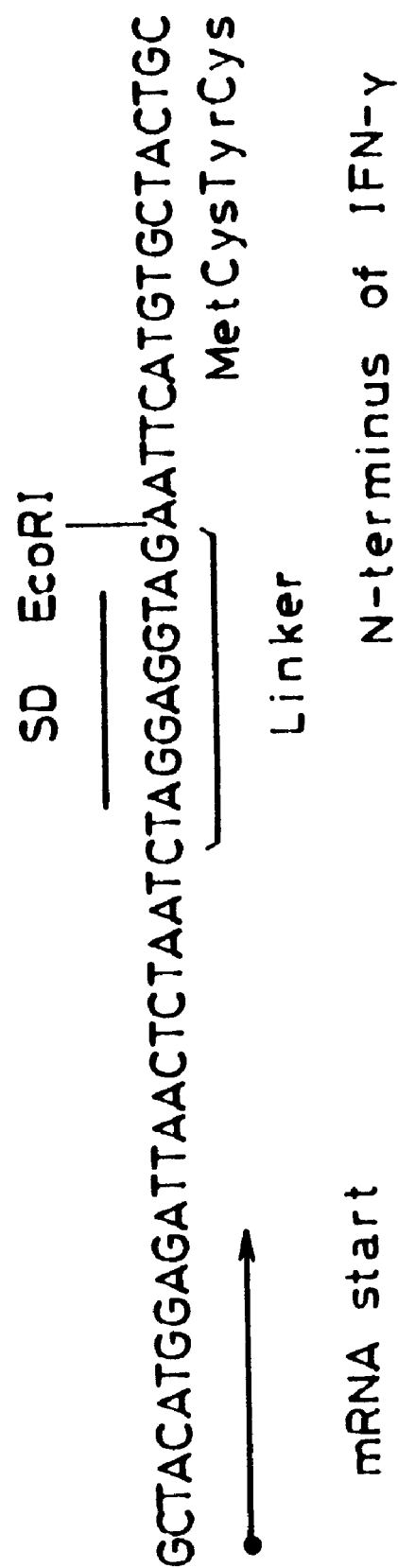

The base sequence of pIN4GIF54 at and around the promoter is shown in FIG. 4. In this pIN4GIF54, the Shine-Dalgarno (SD) sequence is the same as that in pINIA2 and the distance between the SD sequence and the translation initiation codon ATG for hIFN-γ is 9 b.p., which is the same as in pINIA2. Nevertheless, owing to the EcoRI cleavage site introduced between the SD sequence and translation initiation codon ATG, modification of the SD sequence and of the distance between the SD sequence and translation initiation codon can be made with ease and therefore this vector is considered to be an advantageous vector for use in constructing high expression vectors not only for the hIFN-γ gene but also for other genes.

B) Transformation of Escherichia coli W3110

The pIN4GIF54 plasmid obtained was used for transformation of Escherichia coli by the above-mentioned method. Ampicillin-resistant strains were isolated and one of the transformants was named W3110/pIN4GIF54. This transformant was tested for antiviral activity.

III. Test of transformant W3110/pIN4GIF54 for antiviral activity

For examining the amount of hIFN-γ expressed, W3110/pIN4GIF54 and, for comparison, W3110/pGIF54 (essentially the same strain as the transformant disclosed in Japanese Patent Application No. 86,180/1982 and deposited with the Fermentation Research Institute under Deposit No. 6552) were cultivated in the manner mentioned below and the culture supernatants were assayed for antiviral activity. The host strain W3110 was used as a control.

The strains W3110/pIN4GIF54 and W3110 were cultivated in 2.0 ml of L-broth containing 40 μg/ml of ampicillin at 37° C. overnight, 0.1 ml of the culture broth was used for inoculation of 5 ml of L-broth, and incubation was performed at 37° C. for 4 hours. With W3110/pGIF54, 0.1 ml of a preculture broth was used for inoculation of 5 ml of the same L-broth as above, incubation was conducted at 37° C. for 2 hours, then isopropyl-β-D-thiogalactopyranoside (hereinafter abbreviated as IPTG) was added in a final concentration of 1 mM and the incubation was continued for further 2 hours.

Cells were harvested by centrifuging 4 ml of each culture broth at 3,000 rpm for 15 minutes. To the cells obtained, there was added 200 μl of 0.15M sodium phosphate buffer, 50 mM NaCl, pH 7.2, containing 1 mg/ml of lysozyme (Sigma, USA) (hereinafter abbreviated as 1 X PBS). The mixture was allowed to stand on an ice bath for 30 minutes to thereby effect bacteriolysis. Thereafter, the lysate was frozen quickly with dry ice-methanol and then thawed quickly in a constant-temperature bath maintained at 37° C. After disintegration of the cells by three repetitions of such freezing and thawing treatment, the lysate was centrifuged at 10,000 rpm for 10 minutes, and the supernatant was assayed for antiviral activity by the method described in Japanese Patent Application No. 86,180/1982.

The results thus obtained are shown in Table 1.

TABLE 1

Antiviral activity of transformants

| Strain | Antiviral activity I. u./ml |
|---|---|
| W3110 | 0 |
| W3110/pGIF54 | 400 |
| W3110/pIN4GIF54 | 1000 |

The antiviral activity was completely lost at pH 2. Neutralization with a hIFN-γ-specific antibody also resulted in complete inactivation, whereas antibodies specific to α-type and β-type interferons practically failed to cause inactivation.

As seen in Table 1, W3110/pIN4GIF54 showed 2.5 times higher antiviral activity as compared with W3110/pGIF54. However, the degree of expression cannot yet be said to be satisfactory. Therefore, the lipoprotein SD sequence was modified. The lipoprotein SD sequence is GAGG (4 bp) and this sequence is complementary to the sequence CUCC (indicated below by ●●●● of the 3'-terminal 3'AUUC C̈ÜC̈C̈ÄG5' of Escherichia coli 16S ribosome RNA.

The inventors expected that conversion of the lipoprotein SD sequence complementary to said 16S ribosome RNA to AGGAGGT which is used in the R17A or MS2A protein SD sequence might result in an increase in complementarity with 16S ribosome RNA, hence in translation activity, so that the expression of the hIFN-γ protein could be increased.

Therefore, they attempted to insert the SD sequence AGGAGGT between the XbaI-EcoRI sites of the plasmid pIN4GIF54. For that purpose, an oligonucleotide having the above sequence as well as XbaI and EcoRI cohesive ends at the 5'-ends, namely

C T A G G A G G T A G

C T C C A T C T T A A and this was inserted between XbaI-EcoRI of pIN4GIF54, whereby the plasmid pIN5GIF54 was constructed (cf. FIG. 4).

THe following are the details.
IV. Construction of pIN5GIF54 plasmid (cf. FIG. 4)
A) Preparation of oligonucleotide having XbaI and EcoRI cohesive ends The oligonucleotide having the SD sequence AGGAGGT and XbaI and EcoRI cohesive ends at the 5'-ends, namely

5'C T A G G A G G T A G3'

3'C T C C A T C T T A A5' was synthesized by the solid phase method mentioned above (cf. U.S. patent application Ser. No. 496,176). The above oligonucleotide (100 picomoles) was phosphorylated at the 5'-OH, at 37° C. for 60 minutes, in 50 μl of the kinase reaction solution (detailedly described in Example I-C) with 2 units of T4 polynucleotide kinase (Takara Shuzo) added, as mentioned above.

B) Preparation of XbaI-EcoRI DNA fragment of pIN4GIF54 pIN4GIF54 (2.5 μg) was digested with 5 units each of XbaI and EcoRI in 30 μl of 1 X TA solution at 37° C. for 60 minutes for cleaving the DNA. After cleavage, 0.7% agar gel electrophoresis was carried out and an XbaI-EcoRI DNA fragment of about 4.3 Kb (SD sequence-free longer fragment) was eluted from the gel by electrophoresis as mentioned above. The eluate was subjected to phenol treatment and ethanol precipitation as mentioned above and, to the ethanol precipitate, 10 μl of distilled water was added for dissolution of the DNA fragment.

C) Construction of pIN5GIF54

The plasmid pIN5GIF54 was constructed by ligating the above two DNA fragments in the following manner. Thus, to 5 μl a solution of the phosphorylated oligonucleotide (10 picomoles), there were added 3 μl of the ligation reaction solution 10-fold in concentration (mentioned hereinbefore), 10 μl of 100 mM DTT and 4 mM ATP in distilled water, and 1 μl (5 units) of T4 DNA ligase (Boehringer Mannheim). The mixture was incubated at 16° C. overnight.

V. Transformation of Escherichia coli
A) Transformation of Escherichia coli WA802

In the same manner as above (Example II-A), cells of Escherichia coli WA802 as grown in L-broth were treated with CaCl$_2$, and 0.2 ml of cell suspension was mixed with the ligation reaction mixture obtained in Example IV-C for effecting transformation of Escherichia coli WA802. Transformant selection was conducted using a nutrient agar medium (BBL) containing 40 μg/ml of ampicillin. Using one of the transformant strains thus obtained, plasmid separation was performed by the conventional method (cf. Example II-A), and the DNA base sequence at and around the insert region, namely XbaI-EcoRI region, was analyzed. As shown in FIG. 5, pIN5GIF54 must be free of the XbaI cleavage site originally present in pIN4GIF54 (FIG. 3). Therefore, the plasmid separated was treated with XbaI, followed by 0.7% agar gel electrophoresis and determination, for the plasmid DNA remaining uncleaved with XbaI, of the DNA sequence at and around the oligonucleotide fragment insert by the Maxam-Gilbert method. The results obtained confirmed the presence of the intended DNA base sequence. This plasmid was named pIN5GIF54, and the WA802 strain transformed therewith was named WA802/pIN5GIF54.

B) Transformation of Escherichia coli W3110

The pIN5GIF54 plasmid obtained above was used for transformation of Escherichia coli W3110 in the same manner as above. An ampicillin-resistant transformant was isolated and named W3110/pIN5GIF54. This transformant was compared with W3110/pIN4GIF54 with respect to antiviral activity.

VI. Test of W3110/pIN4GIF54 and W3110/pIN5GIF54 for antiviral activity

W3110/pIN4GIF54, W3110/pIN5GIF54 and, as a control, W3110 were each grown in 2.0 ml of L-broth (containing 40 μg/ml of ampicillin) at 37° C. overnight, and 0.1 ml of each culture broth was used for inoculating 5 ml of L-broth (containing 40 μg/ml of ampicillin), followed by further cultivation for 2 hours. A 2-ml portion of each culture broth was centrifuged at 3,000 rpm for 15 minutes. To the cells thus obtained was added 1.0 ml of 1 X PBS containing 1 mg/ml of lysozyme, and the mixture was allowed to stand for 30 minutes to effect bacteriolysis. Thereafter, the cells were disintegrated by three respective repetitions of rapid freezing with dry ice-methanol and rapid thawing at 37° C., and the supernatant obtained by centrifugation at 10,000 rpm for 10 minutes was assayed for antiviral activity by the method described in U.S. patent application Ser. No. 496, 176. The results thus obtained are shown in Table 2.

TABLE 2

Antiviral activity measurement

| Strain | I. u. /ml |
|---|---|
| W3110 | 0 |
| W3110/pIN4GIF54 | 1000 |
| W3110/pIN5GIF54 | 4000 |

As is evident from Table 2, W3110/pIN5GIF54 exhibited 4 times higher antiviral activity as compared with W3110/pIN4GIF54, indicating that the improvement in the SD sequence had been effective in increasing the expression yield of hIFN-γ protein.

*Escherichia coli* W311D transformed by plasmids PIN5T4 and PIN5T5 wherein tetracycline-resistant gene (Tc$^r$) is inserted instead of ampicillin-resistant gene (Ap$^r$) on PIN5GIF54 exhibited the same antiviral activity as W3110/PIN5GIF54 mentioned above.

PIN5T4 was prepared by the ligation of DNA fragment containing hIFN-γ gene and DNA fragment containing Tc$^r$ gene with T4DNA ligase after making the cohesive ends to smooth ends with T4DNA polymerase and dNTP. The former DNA fragment was obtained by cleaving PIN5GIF54 with restriction enzymes AatII and SalI, and the latter by cleaving pBR322 with EcoRI and AhaIII (FIG. 7).

PIN5T5 was able to be prepared by the same procedure as above except for cleaving pBR322 with EcoRI and PstI (FIG. 8).

The antiviral activity disappeared upon treatment at pH 2 and upon neutralization with a hIFN-γ-specific antibody. These facts clearly indicate that these transformants are hIFN-γ-producing strains.

We claim:

1. An *Escherichia coli* plasmid vector which contains a 5'-terminal untranslatable region, said region being inclusive of a promotor region of the *Escherichia coli* lipoprotein gene wherein said promotor region is as shown in FIG. 1, and of a Shine-Dalgano sequence consisting of 5' AGGAGGT 3' at the corresponding originally occurring location in the lipoprotein operon, and of an EcoRI restriction cleavage sequence between the Shine-Dalqano sequence and the translation initiation codon ATG, and a gene chemically synthesized coding for human immune interferon containing the following nucleotide sequence and inserted directly downstream from the ECORI restriction cleavage sequence:

```
              1                                        10
       Met Cys Tyr Cys Gln Asp Pro Tyr Val Lys Glu
    5' ATG TGC TAC TGC CAG GAC CCA TAC GTG AAG GAA
    3' TAC ACG ATG ACG GTC CTG GGT ATG CAC TTC CTT

20
       Ala Glu Asn Leu Lys Lys Tyr Phe Asn Ala Gly
       GCT GAA AAC CTG AAG AAA TAC TTC AAC GCT GGT
       CGA CTT TTG GAC TTC TTT ATG AAG TTG CGA CCA

30
       His Ser Asp Val Ala Asp Asn Gly Thr Leu Phe
       CAT TCT GAC GTT GCT GAC AAC GGT ACT CTG TTC
       GTA AGA CTG CAA CGA CTG TTG CCA TGA GAC AAG

40
       Leu Gly Ile Leu Lys Asn Trp Lys Glu Glu Ser
       CTG GGT ATC CTG AAA AAC TGG AAA GAA GAA TCT
       GAC CCA TAG GAC TTT TTG ACC TTT CTT CTT AGA

50
       Asp Arg Lys Ile Met Gln Ser Gln Ile Val Ser
       GAC CGT AAA ATC ATG CAG TCT CAG ATC GTT TCT
       CTG GCA TTT TAG TAC GTC AGA GTC TAG CAA AGA

60
       Phe Tyr Phe Lys Leu Phe Lys Asn Phe Lys Asp
       TTC TAC TTC AAG CTG TTC AAA AAC TTC AAG GAC
       AAG ATG AAG TTC GAC AAG TTT TTG AAG TTC CTG

70
       Asp Gln Ser Ile Gln Lys Ser Val Glu Thr Ile
       GAC CAG TCT ATC CAG AAA TCT GTT GAA ACT ATC
       CTG GTC AGA TAG GTC TTT AGA CAA CTT TGA TAG

80
       Lys Glu Asp Met Asn Val Lys Phe Phe Asn Ser
       AAG GAA GAC ATG AAC GTT AAG TTC TTC AAC TCT
       TTC CTT CTG TAC TTG CAA TTC AAG AAG TTG AGA

90
       Asn Lys Lys Lys Arg Asp Asp Phe Glu Lys Leu
       AAC AAG AAA AAG CGT GAC GAC TTC GAA AAG CTT
       TTG TTC TTT TTC GCA CTG CTG AAG CTT TTC GAA

100
       Thr Asn Tyr Ser Val Thr Asp Leu Asn Val Gln
       ACT AAC TAC TCT GTT ACT GAC CTT AAT GTA CAG
       TGA TTG ATG AGA CAA TGA CTG GAA TTA CAT GTC 110                                      120
       Arg Lys Ala Ile His Glu Leu Ile Gln Val Met
       CGT AAA GCT ATC CAT GAA CTG ATC CAG GTT ATG
       GCA TTT CGA TAG GTA CTT GAC TAG GTC CAA TAC

130
       Ala Glu Leu Ser Pro Ala Ala Lys Thr Gly Lys
       GCT GAA CTC TCC CCG GCT GCT AAA ACT GGT AAG
       CGA CTT GAC AGG GGC CGA CGA TTT TGA CCA TTC

140
       Arg Lys Arg Ser Gln Met Leu Phe Arg Gly Arg
       CGT AAA AGA TCT CAG ATG CTG TTC CGT GGT CGT
       GCA TTT TCT AGA GTC TAC GAC AAG GCA CCA GCA

146
       Arg Ala Ser Gln Stp
       CGT GCT TCT CAG TAA
       GCA CGA AGA GTC ATT.
```

2. A plasmid vector as set forth in claim 1, which is pIN5GIF54, pIN5T4 or pIN5T5.

3. An *Escherichia coli* transformant obtained by transformation with the plasmid as set forth in claim 1.

4. A transformant as set forth in claim 3, which is WA802/pIN5GIF54, W3110/pIN5GIF54, WA802/pIN5T4, W3110/pIN5T4, WA802/pIN5T5 or W3110/pIN5T5.

5. A culture containing human immune interferon, said culture being obtained by cultivating an *Escherichia coli* transformant as set forth in claim 3 under conditions in which human immune interferon is produced.

6. A method for producing human immune interferon comprising cultivating an *Escherichia coli* transformant as set forth in claim 3 under conditions in which human immune interferon is produced.

7. The *Escherichia coli* transformant WA802/PGIF4, having International Deposit No. BP-282.

* * * * *